United States Patent [19]

Schneebaum et al.

[11] Patent Number: 5,386,818

[45] Date of Patent: Feb. 7, 1995

[54] LAPAROSCOPIC AND ENDOSCOPIC INSTRUMENT GUIDING METHOD AND APPARATUS

[76] Inventors: Cary W. Schneebaum, 230 Brinckerhoff Ct., Englewood, N.J. 07631; Peter J. Wilk, 185 West End Ave., New York, N.Y. 10023

[21] Appl. No.: 59,629

[22] Filed: May 10, 1993

[51] Int. Cl.⁶ .................................................. A61B 1/00
[52] U.S. Cl. ...................................... 128/4; 604/281
[58] Field of Search ............... 128/4, 6, 751, 5, 772, 128/95, 20; 606/108, 205, 170, 171, 198; 604/281, 107

[56] References Cited

U.S. PATENT DOCUMENTS

| | | | |
|---|---|---|---|
| 4,741,326 | 5/1966 | Sidall et al. | 128/4 |
| 4,949,706 | 8/1990 | Thon | 128/4 |
| 5,106,369 | 4/1992 | Christmas | 128/20 X |
| 5,109,830 | 5/1992 | Cho | 128/4 |
| 5,273,026 | 12/1993 | Wilk | 128/20 |

FOREIGN PATENT DOCUMENTS

| | | | |
|---|---|---|---|
| 2800362 | 7/1978 | Germany | 128/6 |

*Primary Examiner*—Richard J. Apley
*Assistant Examiner*—Beverly A. Meindl
*Attorney, Agent, or Firm*—R. Neil Sudol; Henry D. Coleman

[57] ABSTRACT

In an endoscopic or laparoscopic instrument assembly, an elongate tubular instrument guide is inserted into a biopsy channel of an endoscope or laparoscope. The tubular instrument guide is provided with a distal end portion having a spring bias tending to form the distal end portion into an arcuate configuration. The tubular instrument guide is longitudinally slidable in the biopsy channel, whereby the distal end portion may be alternately maintained in a relatively straightened configuration in a distal end of the biopsy channel and moved outside of the biopsy channel to assume the arcuate configuration. An elongate flexible endoscopic or laparoscopic instrument is slidably inserted into the tubular instrument guide so that an operative tip at a distal end of the instrument may project outwardly from the distal end portion upon an ejection of at least a part of the distal end portion of the tubular instrument guide from the biopsy channel.

17 Claims, 2 Drawing Sheets

LAPAROSCOPIC AND ENDOSCOPIC INSTRUMENT GUIDING METHOD AND APPARATUS

BACKGROUND OF THE INVENTION

This invention relates to a method and an associated device utilizable in medical procedures to facilitate the guiding of an instrument to a surgical site. The method and the associated device are particularly useful in laparoscopic and/or endoscopic procedures.

In obtaining a biopsy of esophageal tissues via an end-viewing endoscope, the distal end of the scope must be turned to the side to aim the instrument in the direction of the tissues to be sampled. However, this procedure is frequently difficult owing to the narrowness of the esophagus. Although a side-viewing endoscope can be used to obtain an esophageal biopsy, the scope is nearly useless in examining the stomach, thus necessitating both an end-viewing endoscope and a side-viewing endoscope. Accordingly, a need exists for a device to facilitate the obtaining of an esophageal biopsy via an end-viewing endoscope.

Some endoscopes include two separate biopsy channels for the simultaneous insertion of multiple endoscopic instruments. In addition, U.S. Pat. Nos. 5,025,778 and 4,646,722 to Silverstein et al. disclose the application, to endoscope insertion members, of removable sheaths having expandable biopsy channels. Such endoscope sheaths enable any existing endoscope to be retrofitted to have multiple biopsy channels. Such multiple biopsy channels, however, cannot be used to their full potential, without the existence of flexible endoscopic instruments with distal end portions which can be turned or directed by an operator at the proximal ends of the instruments. One solution is to provide each endoscopic instrument with its own set of orientation control cables. Although this solution is certainly feasible, a less expensive solution would be beneficial.

Individual control of the orientations of the distal ends of laparoscopic instruments would also serve to enhance laparoscopic surgery. Some laparoscopes have biopsy channels which may be used for the insertion of an operating instrument.

OBJECTS OF THE INVENTION

An object of the present invention is to provide a device utilizable with an endoscope and/or laparoscope for facilitating the guiding of an endoscopic or laparoscopic instrument to a surgical or diagnostic site.

A related object of the present invention is to provide a method for facilitating the performance of a surgical operation, e.g., the taking of a biopsy, via an endoscope or laparoscope.

Another, more particular, object of the present invention is to provide such a device which is inexpensive to manufacture and easy to use.

A further object of the present invention is to provide a method and/or an associated instrument assembly or apparatus for use in directing the distal end of an endoscopic or laparoscopic insertion tube.

Another specific object of the present invention is to provide such a method and/or an associated instrument assembly or apparatus which reduces the costs of endoscopes.

These and other objects of the present invention will be apparent from the drawings and detailed descriptions herein.

SUMMARY OF THE INVENTION

An endoscopic or laparoscopic instrument assembly comprises, in accordance with the present invention, an insertion tube provided with a biopsy channel and an elongate tubular member inserted into the biopsy channel, the tubular member being provided with a distal end portion having a spring bias tending to form the distal end portion into an arcuate configuration. The tubular member is longitudinally slidable in the biopsy channel, whereby the distal end portion may be alternately maintained in a relatively straightened configuration in a distal end of the biopsy channel and moved outside of the biopsy channel to assume the arcuate configuration. An elongate flexible endoscopic or laparoscopic instrument is slidably inserted into the tubular member so that an operative tip at a distal end of the instrument may project outwardly from the distal end portion upon an ejection of at least a part of the distal end portion of the tubular member from the biopsy channel.

According to another feature of the present invention, the assembly further comprises componentry on the tubular member for enabling a turning of the distal end portion about an axis extending substantially parallel to the biopsy channel at the distal end thereof. This componentry may merely comprise a reinforcement strip or rod attached to the tubular member and extending longitudinally therealong, the reinforcement rod being bendable but not twistable. Other, equivalent structures are available to those skilled in the art for enabling a rotation of the distal end portion of the tubular member about a longitudinal axis.

The insertion tube of the endoscope or laparoscope may be provided with a removable sheath, the biopsy channel being an expandable collapsed channel provided in the sheath. In that event, the tubular member is advantageously inserted into the biopsy channel subsequently to the introduction of the endoscopic or laparoscopic insertion tube into the patient.

A device for use in medical procedures comprises, in accordance with the present invention, a tubular member insertable through a biopsy channel of an endoscope or laparoscope, the tubular member having a distal end portion provided with a spring bias tending to form the distal end portion into an arcuate configuration, e.g., a substantially U-shaped configuration.

According to a further feature of the present invention, a rotation element is provided on the tubular member for enabling a rotating of the distal end portion relative to a longitudinal axis by manipulating a proximal end of the tubular member.

A method for use in endoscopic or laparoscopic procedures comprises, in accordance with the present invention, the steps of (a) providing an insertion tube having a biopsy channel, (b) providing an elongate tubular member insertable into the biopsy channel, the tubular member being formed with a distal end portion having a spring bias tending to form the distal end portion into an arcuate configuration, (c) providing an elongate flexible endoscopic or laparoscopic instrument slidably insertable into the tubular member, the instrument having an operative tip at a distal end, (d) inserting a distal end segment of the insertion tube into a patient, and (e) pushing the tubular member in a distal direction to eject at least a part of the distal end portion from the biopsy channel upon at least partial insertion of the insertion tube into a patient, thereby enabling the part of the distal end portion to bend under the action of the spring bias. Subsequent steps include (f) moving the instrument in a distal direction through the tubular member to eject the operative tip from the tubular member, whereby the operative tip projects from the tubular member in a direction determined at least in part by a curvature of the projecting distal part of the tubular member, and (g) operating on internal tissues of the patient with the operative tip.

According to more specific features of the present invention, the method further comprises the step of disposing a portion of the tubular member inside the biopsy channel prior to the introduction of the insertion tube into the patient. This step is particularly useful where the biopsy channel is a permanent part of the endoscope or laparoscope insertion member. In addition, the endoscopic or laparoscopic instrument may be inserted into the tubular member prior to the disposition of the tubular member inside the biopsy channel of the insertion tube. Alternatively, the endoscopic or laparoscopic instrument may be inserted into the tubular member only upon at least partial disposition of the tubular member inside the biopsy channel of the endoscopic or laparoscopic insertion member.

Especially where the biopsy channel is a collapsed channel on a removable sheath, the tubular member is inserted into the biopsy channel subsequently to the introduction of the endoscopic or laparoscopic insertion tube into the patient.

Where the endoscopic or laparoscopic insertion tube is flexible and provided with actuator means for controlling a distal end orientation of the insertion tube, the method further comprises the step of operating the actuator means to turn a distal end of the insertion tube upon at least partial insertion of the insertion tube into the patient.

The moving of the endoscopic or laparoscopic instrument in the distal direction to eject the operative tip from the distal end of the tubular member may be done either before or after the ejection of the distal end portion of the tubular member from the biopsy channel. Of course, the extent that the instrument projects from the distal end of the tubular member may be modified during the course of a procedure as circumstances require.

It is to be noted that the extent to which the tubular member projects from the distal end of the biopsy channel will determine the angle between the distal end portion of the tubular member and the axis of the endoscopic or laparoscopic insertion tube at the distal end thereof. Thus, to control the orientation of the instrument with respect to the endoscope or laparoscope, the operator controls the degree of insertion of the tubular member into the biopsy channel.

A device and method in accordance with the present invention greatly facilitates the performance of endoscopic and/or laparoscopic surgery by facilitating the guiding of an endoscopic or laparoscopic instrument to a surgical site.

A variation in the above-described method for use in endoscopic or laparoscopic procedures comprises, in accordance with the present invention, the steps of (i) providing an insertion tube having a channel and formed with a distal end portion having a spring bias tending to form the distal end portion into an arcuate configuration, (ii) providing an elongate tubular sheath member, (iii) inserting the insertion tube into the sheath member so that the distal end portion of the insertion tube is maintained in a substantially straightened configuration, (iv) inserting a distal end segment of the insertion tube with the sheath member into a patient, and (v) pushing the insertion tube in a distal direction relative to the sheath member upon insertion of the distal end segment into a patient, to eject at least a part of the distal end portion from the sheath member, thereby enabling the part of the distal end portion to bend under the action of the spring bias.

In an optional step of the method, used in placing the endoscope insertion tube in a patient and performed after the ejection of the insertion tube from the sheath, the insertion tube and the sheath member are together moved in a distal direction, while maintaining the insertion tube and the sheath member in substantially fixed relation to one another, thereby constraining the insertion tube and the sheath member to follow the bent part of the distal end portion.

Alternatively, the endoscope insertion tube may be pushed along a bend in an organ of the patient, while the sheath remains essentially fixed relative to the patient. Upon the negotiation of the bend, the sheath is pushed in the distal direction while the endoscope insertion member is maintained in position.

This variation in the method of the invention enables construction of a cheaper endoscope insertion tube, wherein turning of the endoscope to negotiate turns in an internal organ such as an intestine is accomplished by moving the sheath and the endoscope insertion member relative to one another to enable an inherent bending of the distal end portion of the endoscope insertion member. To that end, the endoscope insertion member may be provided with one or more longitudinally extending embedded metal rods each having an inherent spring bias tending to bend the distal end portion of the endoscope.

This construction and technique reduces the cost of an endoscope inasmuch as the more costly cables of conventional endoscopes are eliminated. The directing of the distal end portion of the endoscope insertion tube during an endoscopic operation, to juxtapose the distal end of the endoscope to a desired surgical site, is also accomplished by essentially the same procedure.

DETAILED DESCRIPTION

Figure 1:
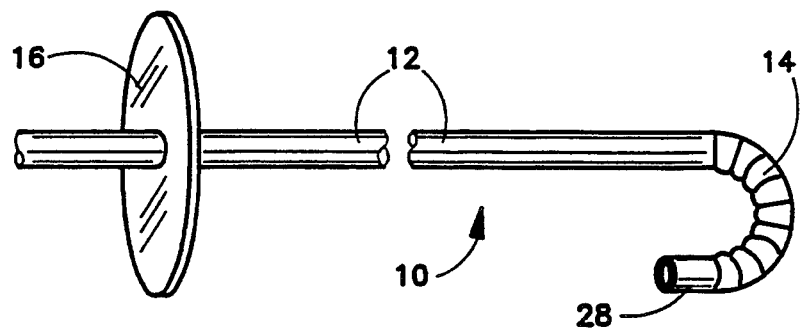
FIG. 1 is a partial schematic side perspective view, on an enlarged scale, of a device in accordance with the present invention for guiding the distal ends of flexible endoscopic or laparoscopic instruments upon ejection of those ends from biopsy channels during endoscopic or laparoscopic procedures.

As illustrated in FIG. 1, a device 10 for use in endoscopic and/or laparoscopic medical procedures comprises a tubular member 12 having a distal end portion 14 provided with a spring bias or memory tending to form the distal end portion into an arcuate configuration, e.g., a substantially U-shaped configuration. At a proximal end, tubular member 12 is provided with a flange or other hand grip 16 for facilitating use of the device as described in detail hereinafter.

Figure 2:
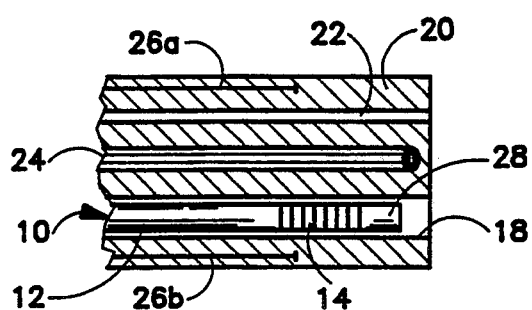
FIG. 2 is a partial schematic cross-section view of a distal end of an endoscope, showing the device of FIG. 1 in a straightened configuration inside a biopsy channel of the endoscope.

As illustrated in FIG. 2, tubular member 12 is insertable through a biopsy channel 18 of an endoscope or laparoscope insertion tube 20 also provided with a fiber-optic illumination guide 22, a fiber-optic image guide 24, and tensioning cables 26a and 26b for controlling the orientation of the distal end of insertion tube 20.

Tubular member 12 is longitudinally slidable in biopsy channel 18. Accordingly, distal end portion 14 of tubular member 12 may be maintained in a relatively straightened configuration (FIG. 2) in a distal end section of biopsy channel 18 during insertion and removal of endoscopic or laparoscopic insertion tube 20 from a patient (not shown). Upon the arrival of the distal end of insertion tube 20 at a surgical or diagnostic site inside the patient, tubular member 12 is shifted in the distal direction through biopsy channel 18 until a part of distal end portion 14 of the tubular member emerges from the biopsy channel and bends under the action of the internal spring force built into tubular member 12.

Figure 3A:
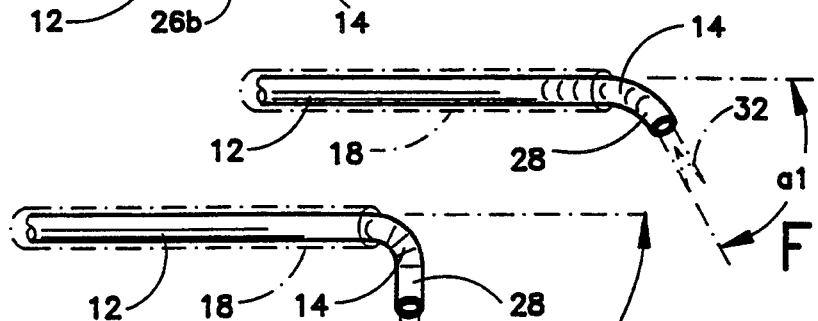
FIGS. 3A–3C are partial schematic side perspective views, on an enlarged scale, of the device of FIG. 1, showing successive orientations of a distal end portion of the device upon increasing emergence of the device from the distal end of the endoscope biopsy channel of FIG. 2.
Figure 3B:
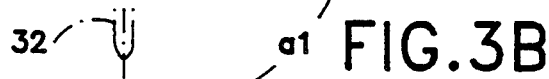

As illustrated in FIGS. 3A–3B, the degree of bending of distal end portion 14 of tubular member 12 is determined by controlling the degree of ejection of distal end portion 14 from biopsy channel 18. The more tubular member 12 is pushed in the distal direction, the greater the angle al that a tip 28 of tubular member 12 bears with respect to a longitudinal axis of biopsy channel 18.

Figure 3C:
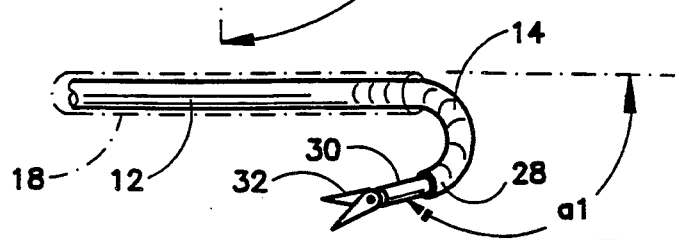

Upon the attainment of a desired angle al, an elongate flexible endoscopic or laparoscopic instrument 30 is slidably inserted through tubular member 12 so that an operative tip 32 at a distal end of the instrument projects outwardly from distal end portion 14. Thus, tubular member 12 serves as an instrument guide for controlling the orientation of operative tip 32 with respect to endoscopic or laparoscopic insertion tube 20. As illustrated in dot-dash lines in FIGS. 3A–3C, instrument 30 may be moved through tubular member 12 prior to the ejection of distal end portion 14 of tubular member 12 from biopsy channel 18. In that procedure, operative tip 32 projects from tip 28 prior to selection of the orientation angle al. This procedure will aid the selection of orientation angle al at least in some circumstances. Of course, the degree of projection of instrument 30 from tubular member 12 may be varied after the partial ejection of distal end portion 14 of tubular member 12 from biopsy channel 18. Similarly, tubular member 12 may be alternately shifted in proximal and distal directions to select an optimal orientation angle al prior to the operating of instrument 30 to act on organic internal tissues of a patient.

It is to be noted that instrument 30 may be virtually any endoscopic or laparoscopic instrument, including, but not limited to, biopsy forceps, graspers, scissors, cauterization snare and probe, irrigation tube, or laser guide.

Figure 4:
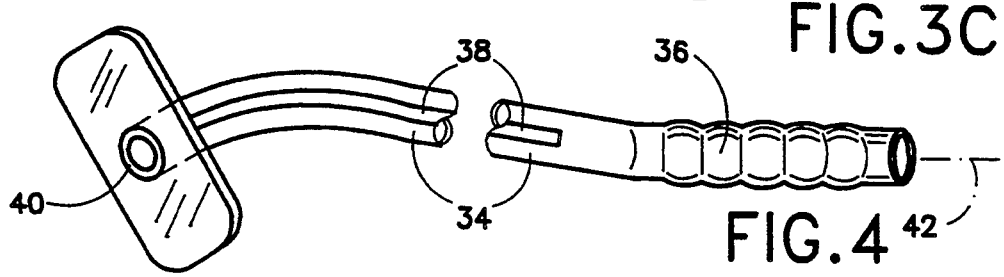
FIG. 4 is a partial schematic side perspective view, on a substantially enlarged scale, of another device in accordance with the present invention for guiding the distal ends of flexible endoscopic or laparoscopic instruments upon ejection of those ends from biopsy channels during endoscopic or laparoscopic procedures.

FIG. 4 depicts a tubular endoscopic or laparoscopic instrument guide 34 having a distal end portion 36 provided with an internal spring bias or memory tending to form the distal end portion into an arcuate configuration (not shown). Tubular member 34 is provided with at least one longitudinally extending torsion strip or reinforcement rod 38 for transmitting a torque from a proximal end 40 of tubular member 34 to distal end portion 36 thereof, thereby enabling an operator to turn distal end portion 36 about an axis 42 extending substantially parallel to an endoscope or laparoscope biopsy channel at the distal end thereof. Strip or rod 38 is bendable about transverse axes but not twistable about a longitudinal axis (parallel to axis 42).

It is to be noted that the tubular endoscopic or laparoscopic instrument guide members 12 and 34 as described herein may be inserted into a collapsed biopsy channel provided in a sheath which is removably attached to an endoscopic insertion tube. Such a sheath is known from U.S. Pat. Nos. 5,025,778 and 4,646,722 to Silverstein et al., the disclosures of which are hereby incorporated by reference. The introduction of the instrument guide members 12 and 34 may be effectuated subsequently to the introduction of the endoscopic insertion tube into a patient.

Figure 5A:
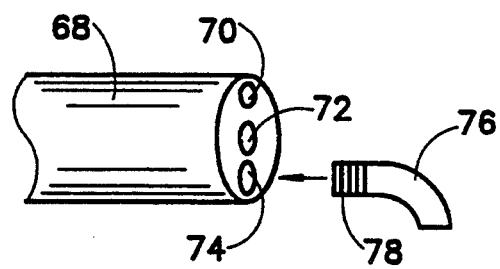
FIGS. 5A and 5B are schematic partial perspective views of an endoscope insertion member before and after attachment of an instrument guide to the distal end of a biopsy channel, in accordance with the present invention.
Figure 5B:
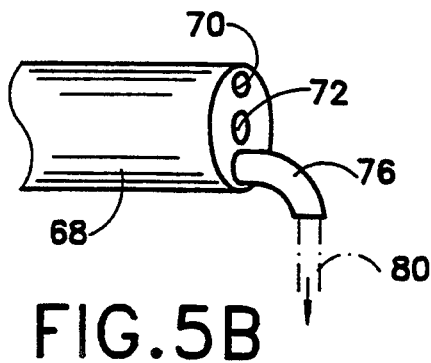

As illustrated in FIGS. 5A and 5B, an endoscopic or laparoscopic insertion member 68 having an illumination guide 70, an image guide 72, and a biopsy channel 74 is provided with a permanently arcuate instrument guide member 76 which is screwed via threads 78 to the distal end of biopsy channel 74 prior to introduction of insertion member 68 into a patient. The distal end of an endoscopic or laparoscopic instrument 80 projects in a direction determined by the angle of member 76.

Figure 6:
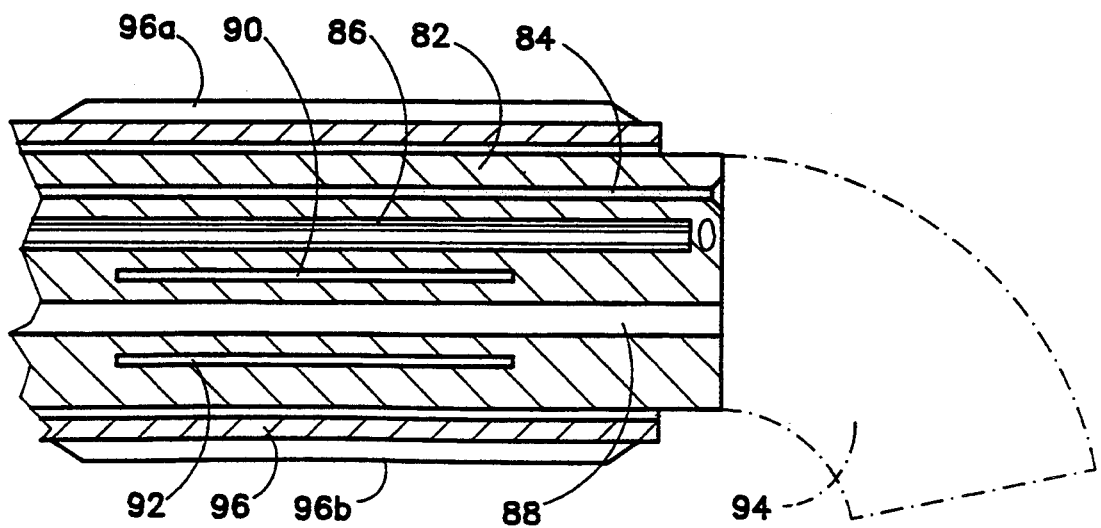
FIG. 6 is a partial schematic cross-section view of a distal end of an endoscope insertion member with embedded spring biasing rods in accordance with the present invention, the endoscope insertion member being surrounded by a sheath for use in a method in accordance with the present invention.

As illustrated in FIG. 6, an endoscope assembly comprises an endoscope insertion tube 82 longitudinally traversed by a fiber-optic illumination guide 84, a fiber-optic image guide 86, and a biopsy channel 88. Embedded in insertion tube 82 at a distal end thereof are a plurality of rods 90 and 92 each formed with an inherent spring bias tending to bend the generally coextensive distal end portion of endoscope insertion tube 82 into the same arcuate configuration 94. The distal end portion of insertion tube 82 may be maintained in a straightened configuration (solid lines) by a tubular sheath or outer insertion tube 96, in opposition to the bending forces exerted by rods 90 and 92. Upon an ejection of the distal end of insertion tube 82 from the distal end of sheath 96, rods 90 and 92 bend insertion tube 82 into arcuate configuration 94. The direction of bending of insertion tube 82 (e.g., right, left, up, down) may be controlled by rotating the insertion tube about its longitudinal axis from outside the patient. Upon a retraction of insertion tube 82 back inside sheath 96, the tube reassumes its straightened configuration.

The structure of FIG. 6 aids in directing the distal end of endoscope insertion tube 82 towards a desired diagnostic or surgical site inside the patient, for example, along the wall of the colon or stomach. Accordingly, upon the insertion of tube 82 with sheath 96 into a patient so that the distal end of the assembly is proximate to a desired surgical site and upon an ejection of tube 82 from sheath 96, thereby forming arcuate configuration 94, an endoscopic type operating instrument (not shown) with a distal end portion extending from the biopsy channel 88 is used to operate on the organic tissues of the patient at the surgical site.

The endoscopic operating instrument inserted through biopsy channel 88 may be a biopsy forceps, a cauterization snare, an irrigation and/or suction device, a laser-guiding fiber, etc. In one specific embodiment of the procedure, the endoscopic operating instrument is ejected from the distal end of biopsy channel 88 only upon the ejection of the distal end portion of tube 82 from sheath 96 and the consequent formation of arcuate configuration 94. Alternatively, an operative tip of the endoscopic operating instrument may be projecting from biopsy channel 88 prior to the staggering of tube 82 and sheath 96 and the consequent bending of the endoscope insertion tube 82.

The structure of FIG. 6 also facilitates insertion of the endoscope insertion tube 82 into the patient. As with conventional cable systems, the distal end of endoscope insertion tube 82 is bent prior to the negotiation of a turn on an internal organ of the patient by the tube and sheath assembly. The turning or bending of the distal end portion of the endoscope insertion tube 82 aids in directing the tube towards a bend in the organ.

It is to be understood that insertion tube 82, with its inherent distal end spring bent, may be used in conjunction with endoscopic instruments each having their own internal spring bias. In this manner a substantial degree of control in endoscopic type operations may be achieved. An endoscopic instrument with a spring bias inserted through biopsy channel 88 can be used to counteract or enhance the bending forces exerted by rods 90 and 92, whether during placement of an endoscope insertion member or during a subsequent endoscopic operation.

Sheath 96 may be provided with a plurality of circumferentially spaced longitudinally extending ribs 96a and 96b for reinforcing the sheath to facilitate the straightening of the distal end portion of endoscope insertion tube 82 in opposition to the spring forces exerted by rods 90 and 92. Other equivalent sheath reinforcement structures are well within the skill of the art.

Although the invention has been described in terms of particular embodiments and applications, one of ordinary skill in the art, in light of this teaching, can generate additional embodiments and modifications without departing from the spirit of or exceeding the scope of the claimed invention. For example, virtually all laparoscopic instruments may be provided with internal spring biases at their distal ends and further provided with external insertion-tube sheaths for enabling control of the bending of the distal ends, as described herein. In such cases, the shafts of the laparoscopic instruments are considered tubular members even though they be may rods. The tubular laparoscopic instrument shafts and their associated tubular sheaths are inserted together through laparoscopic trocar sleeves. In the case of laparoscopic instruments, the sheaths may be rigid members.

Accordingly, it is to be understood that the drawings and descriptions herein are proferred by way of example to facilitate comprehension of the invention and should not be construed to limit the scope thereof.

What is claimed is:

1. An endoscopic or laparoscopic assembly comprising:

an elongate endoscope or laparoscope insertion tube with a longitudinally extending biopsy channel;

an elongate tubular member inserted into said channel, said tubular member being provided with a distal end portion having an internal spring bias tending to form said distal end portion into an arcuate configuration in the absence of an external straightening force on said distal end portion, said tubular member being longitudinally slidable in said channel, whereby said distal end portion may be alternately maintained in a relatively straightened configuration in a distal end of said channel and moved outside of said channel to assume said arcuate configuration; and an elongate flexible endoscopic or laparoscopic instrument having an operative tip, said instrument being slidably inserted into said tubular member so that said operative tip may project outwardly from said distal end portion upon an ejection of at least a part of said distal end portion of said tubular member from said channel.

2. The assembly defined in claim 1, further comprising means on said tubular member for enabling a turning of said distal end portion about an axis extending substantially parallel to said channel at said distal end thereof.

3. The assembly defined in claim 1 wherein said insertion tube is provided with a removable sheath, said channel being provided in said sheath.

4. The assembly defined in claim 1 wherein said insertion tube is provided with image transmission guide means for transmitting an image from a distal end of the insertion tube to a proximal end thereof.

5. The assembly defined in claim 1 wherein said insertion tube includes a removable sheath, said channel being provided in said sheath.

6. A device for use in medical procedures, comprising a tubular member insertable through a channel of an endoscope or laparoscope, said tubular member having a distal end portion provided with an internal spring bias tending to form said distal end portion into an arcuate configuration in the absence of an external straightening force on said distal end portion, further comprising means on said tubular member for enabling a rotating of said distal end portion of said tubular member by manipulating a proximal end of said tubular member.

7. The device defined in claim 6 wherein said arcuate configuration is substantially U-shaped.

8. A method for use in endoscopic or laparoscopic procedures, comprising the steps of:

providing an insertion tube having a biopsy channel;

providing an elongate tubular member insertable into said channel, said tubular member being formed with a distal end portion having an internal spring bias tending to form said distal end portion into an arcuate configuration in the absence of an external straightening force on said distal end providing an elongate flexible endoscopic or laparoscopic instrument slidably insertable into said tubular member, said instrument having a distal tip;

inserting a distal end segment of said insertion tube into a patient;

upon insertion of said distal end segment into a patient, pushing said tubular member in a distal direction to eject at least a part of said distal end portion from said channel;

upon ejection of said part of said distal end portion from said channel, bending said part of said distal end portion by action of said internal spring bias; and moving said instrument in a distal direction through said tubular member to eject said distal tip from said tubular member, whereby said distal tip projects from said tubular member in a direction determined at least in part by a curvature of said part of said distal end portion of said tubular member.

9. The method defined in claim 8, further comprising the step of disposing a portion of said tubular member inside said channel prior to said step of inserting.

10. The method defined in claim 9, further comprising the step of inserting said instrument into said tubular member prior to said step of disposing.

11. The method defined in claim 9, further comprising the step of inserting said instrument into said tubular member only upon at least partial completion of said step of disposing.

12. The method defined in claim 8 wherein said tubular member is inserted into said channel subsequently to said step of inserting said insertion tube into the patient.

13. The method defined in claim 8 wherein said insertion tube is flexible and provided with actuator means for controlling a distal end orientation of said insertion tube, further comprising the step of operating said actuator means to turn a distal end of said insertion tube upon insertion of said distal end segment into the patient.

14. The method defined in claim 8 wherein said step of moving is performed subsequently to said step of pushing.

15. The method defined in claim 8 wherein said step of moving is performed prior to said step of pushing.

16. The method defined in claim 8, further comprising the step of rotating at least said distal end portion of said tubular member upon completion of said step of pushing.

17. The method defined in claim 8 wherein said insertion tube is provided with an image transmission guide, further comprising the step of transmitting an image in a proximal direction along said transmission guide, said step of operating including the step of visually monitoring said internal tissues of the patient as presented in said image.

* * * * *

UNITED STATES PATENT AND TRADEMARK OFFICE
CERTIFICATE OF CORRECTION

PATENT NO.    : 5,386,818
DATED         : February 7, 1995
INVENTOR(S)   : Cary W. Schneebaum and Peter J. Wilk It is certified that error appears in the above-indentified patent and that said Letters Patent is hereby corrected as shown below:

Column 8, line 63, insert --portion;-- after "end".

Signed and Sealed this

Twelfth Day of September, 1995

Attest:

BRUCE LEHMAN

*Attesting Officer*    *Commissioner of Patents and Trademarks*